United States Patent
Calderon Oliveras et al.

(10) Patent No.: US 10,463,816 B2
(45) Date of Patent: Nov. 5, 2019

(54) COMPLIANCE-ASSISTING MODULE FOR AN INHALER

(71) Applicant: Norton (Waterford) Limited, Waterford (IE)

(72) Inventors: Enrique Calderon Oliveras, Waterford (IE); Daniel Buck, Waterford (IE); Frederic Scott Fleming, Amstelveen (NL); Douglas E. Weitzel, Hamilton, NJ (US)

(73) Assignee: Norton (Waterford) Limited, Waterford (IE)

( * ) Notice: Subject to any disclaimer, the term of this patent is extended or adjusted under 35 U.S.C. 154(b) by 272 days.

(21) Appl. No.: 15/506,171

(22) PCT Filed: Aug. 28, 2015

(86) PCT No.: PCT/EP2015/069781
§ 371 (c)(1),
(2) Date: Feb. 23, 2017

(87) PCT Pub. No.: WO2016/030521
PCT Pub. Date: Mar. 3, 2016

(65) Prior Publication Data
US 2017/0274163 A1    Sep. 28, 2017

Related U.S. Application Data

(60) Provisional application No. 62/043,120, filed on Aug. 28, 2014.

(51) Int. Cl.
*A61M 15/00* (2006.01)

(52) U.S. Cl.
CPC ...... *A61M 15/0065* (2013.01); *A61M 15/008* (2014.02); *A61M 15/009* (2013.01);
(Continued)

(58) Field of Classification Search
CPC .......... A61M 15/0065; A61M 15/0071; A61M 15/008; A61M 15/0026; A61M 2205/3331; A61M 2205/587
See application file for complete search history.

(56) References Cited

U.S. PATENT DOCUMENTS 5,363,842 A * 11/1994 Mishelevich ........ A61B 8/0875
128/200.14
5,544,647 A    8/1996 Jewett et al.
(Continued)

FOREIGN PATENT DOCUMENTS

EP    0028929 A2    5/1981
EP    1135056 B1    8/2006
(Continued)

OTHER PUBLICATIONS

Wikipedia, "Bluetooth", Available at https://en.wikipedia.org/wiki/Bluetooth, Mar. 3, 2013, 21 pages.
(Continued)

*Primary Examiner* — Bradley J Osinski
(74) *Attorney, Agent, or Firm* — Condo Roccia Koptiw LLP

(57) ABSTRACT

An inhaler includes a mouthpiece cover, a pressure sensor, a first indicator and a second indicator. The first indicator may be configured to indicate based on a state of the cover, and the second indicator may be configured to indicate based on an output of the pressure sensor. For example, when the mouthpiece cover opens, the first indicator may illuminate and a dose of medication may be transferred from a reservoir to a dosing cup. The second indicator may illuminate if an amount of inhaled medication reaches a predetermined threshold for successful inhalation.

20 Claims, 13 Drawing Sheets

(52) U.S. Cl.
CPC .... *A61M 15/0026* (2014.02); *A61M 15/0071* (2014.02); *A61M 15/0091* (2013.01); *A61M 15/00* (2013.01); *A61M 2205/3331* (2013.01); *A61M 2205/3576* (2013.01); *A61M 2205/3584* (2013.01); *A61M 2205/50* (2013.01); *A61M 2205/58* (2013.01); *A61M 2205/583* (2013.01); *A61M 2205/584* (2013.01); *A61M 2205/587* (2013.01); *A61M 2209/088* (2013.01)

(56) References Cited

U.S. PATENT DOCUMENTS

| | | | |
|---|---|---|---|
| 5,758,638 A | 6/1998 | Kreamer et al. | |
| 5,809,997 A | 9/1998 | Wolf et al. | |
| 5,839,429 A | 11/1998 | Marnfeldt et al. | |
| 5,842,468 A | 12/1998 | Denyet et al. | |
| 5,887,586 A | 3/1999 | Dahlback et al. | |
| 6,285,731 B1 | 9/2001 | Marnfeldt et al. | |
| 6,390,088 B1 | 5/2002 | Sprenger et al. | |
| 6,958,691 B1 | 10/2005 | Anderson et al. | |
| 6,978,780 B1 | 12/2005 | Marnfeldt et al. | |
| 6,990,975 B1 | 1/2006 | Jones et al. | |
| 7,072,738 B2 | 7/2006 | Bonney et al. | |
| 7,151,456 B2 | 12/2006 | Godfrey et al. | |
| 7,191,777 B2 | 3/2007 | Brand et al. | |
| 7,198,172 B2 | 4/2007 | Harvey et al. | |
| 7,233,228 B2 | 6/2007 | Lintell et al. | |
| 7,249,687 B2 | 7/2007 | Anderson et al. | |
| 7,318,434 B2 | 1/2008 | Gumaste et al. | |
| 7,331,340 B2 | 2/2008 | Barney et al. | |
| 7,347,200 B2 | 3/2008 | Jones et al. | |
| 7,383,837 B2 | 6/2008 | Robertson et al. | |
| 7,424,888 B2 | 9/2008 | Harvey et al. | |
| 7,495,546 B2 | 2/2009 | Lintell et al. | |
| 7,715,277 B2 | 5/2010 | De La Huerga | |
| 7,837,648 B2 | 11/2010 | Blair et al. | |
| 8,231,573 B2 | 7/2012 | Edwards et al. | |
| 8,240,301 B2 | 8/2012 | Spaargaren et al. | |
| 8,424,517 B2 | 4/2013 | Sutherland et al. | |
| 8,439,033 B2 | 5/2013 | Gumaste et al. | |
| 8,464,707 B2 | 6/2013 | Jongejan et al. | |
| 8,547,239 B2 | 10/2013 | Peatfield et al. | |
| 8,725,291 B2 | 5/2014 | Czaja et al. | |
| 8,807,131 B1 | 8/2014 | Tunnell et al. | |
| 8,960,189 B2 | 2/2015 | Morrison et al. | |
| 8,997,735 B2 | 4/2015 | Zierenberg et al. | |
| 9,056,174 B2 | 6/2015 | Bradshaw et al. | |
| 9,174,009 B2 | 11/2015 | Peatfield et al. | |
| 9,188,579 B2 | 11/2015 | Shen et al. | |
| 9,242,056 B2 | 1/2016 | Andersen et al. | |
| 9,339,616 B2 | 5/2016 | Denny et al. | |
| 9,364,619 B2 | 6/2016 | Overfield et al. | |
| 9,427,534 B2 | 8/2016 | Bruin et al. | |
| 9,463,291 B2 | 10/2016 | Imran et al. | |
| 9,468,729 B2 | 10/2016 | Sutherland et al. | |
| 9,474,695 B1 | 10/2016 | Khalid | |
| 9,550,031 B2 | 1/2017 | Van Sickle et al. | |
| 9,694,147 B2 | 7/2017 | Peatfield et al. | |
| 9,736,642 B2 | 8/2017 | Ostrander et al. | |
| 9,839,398 B2 | 12/2017 | Yamamori et al. | |
| 9,911,308 B2 | 3/2018 | Edwards et al. | |
| 9,956,360 B2 | 5/2018 | Germinario et al. | |
| 9,962,507 B2 | 5/2018 | Germinario et al. | |
| 9,962,508 B2 | 5/2018 | Bruin et al. | |
| 10,016,134 B2 | 7/2018 | Hansen et al. | |
| 10,046,121 B2 | 8/2018 | Kolb et al. | |
| 2002/0185128 A1 | 12/2002 | Theobald et al. | |
| 2003/0192535 A1 | 10/2003 | Christrup et al. | |
| 2004/0050385 A1 | 3/2004 | Bonney et al. | |
| 2004/0089299 A1 | 5/2004 | Bonney et al. | |
| 2004/0117062 A1 | 6/2004 | Bonney et al. | |
| 2005/0119604 A1 | 6/2005 | Bonney et al. | |
| 2005/0161467 A1 | 7/2005 | Jones et al. | |
| 2005/0247312 A1 | 11/2005 | Davies et al. | |
| 2005/0251289 A1 | 11/2005 | Bonney et al. | |
| 2007/0016443 A1 | 1/2007 | Wachman et al. | |
| 2008/0178872 A1* | 7/2008 | Genova ............ A61M 15/0065 128/200.23 |
| 2008/0230057 A1 | 9/2008 | Sutherland et al. | |
| 2009/0221308 A1 | 9/2009 | Lerner et al. | |
| 2010/0242960 A1 | 9/2010 | Zangerle et al. | |
| 2010/0250280 A1 | 9/2010 | Sutherland et al. | |
| 2011/0000481 A1 | 1/2011 | Gumaste et al. | |
| 2011/0162642 A1 | 7/2011 | Akouka et al. | |
| 2011/0282693 A1 | 11/2011 | Craft et al. | |
| 2012/0038226 A1 | 2/2012 | Tran et al. | |
| 2012/0313785 A1 | 12/2012 | Hanson et al. | |
| 2013/0002795 A1 | 1/2013 | Shavelsky et al. | |
| 2013/0030566 A1 | 1/2013 | Shavelsky et al. | |
| 2013/0197693 A1 | 8/2013 | Kamen et al. | |
| 2013/0269685 A1 | 10/2013 | Wachtel et al. | |
| 2014/0106324 A1 | 4/2014 | Adams et al. | |
| 2014/0116426 A1 | 5/2014 | Mullinger et al. | |
| 2014/0137737 A1 | 5/2014 | Wilkinson et al. | |
| 2014/0137744 A1 | 5/2014 | Wilkinson et al. | |
| 2014/0182584 A1 | 7/2014 | Sutherland et al. | |
| 2014/0188348 A1 | 7/2014 | Gautama et al. | |
| 2014/0251330 A1 | 9/2014 | Collins et al. | |
| 2014/0352690 A1 | 12/2014 | Kolb et al. | |
| 2015/0068528 A1 | 3/2015 | Ahmad et al. | |
| 2015/0077737 A1 | 3/2015 | Belinsky et al. | |
| 2015/0137994 A1 | 5/2015 | Rahman et al. | |
| 2015/0283036 A1 | 10/2015 | Aggarwal et al. | |
| 2015/0283341 A1 | 10/2015 | Adams et al. | |
| 2016/0012702 A1 | 1/2016 | Hart et al. | |
| 2016/0082208 A1 | 3/2016 | Ballam et al. | |
| 2016/0128389 A1 | 5/2016 | Lamb et al. | |
| 2016/0166766 A1 | 6/2016 | Schuster et al. | |
| 2016/0213865 A1 | 7/2016 | Poree et al. | |
| 2016/0228657 A1 | 8/2016 | Sutherland et al. | |
| 2016/0256639 A1 | 9/2016 | Van Sickle et al. | |
| 2016/0314256 A1 | 10/2016 | Su et al. | |
| 2017/0079557 A1 | 3/2017 | Lauk et al. | |
| 2017/0109493 A1 | 4/2017 | Hogg et al. | |
| 2017/0140125 A1 | 5/2017 | Hogg et al. | |
| 2017/0164892 A1 | 6/2017 | Sezan et al. | |
| 2017/0173279 A1 | 6/2017 | Sutherland et al. | |
| 2017/0246406 A1 | 8/2017 | Sutherland et al. | |
| 2017/0258993 A1 | 9/2017 | Pizzochero et al. | |
| 2017/0262613 A1 | 9/2017 | Ljungberg et al. | |
| 2017/0325734 A1 | 11/2017 | Sutherland et al. | |
| 2017/0363673 A1 | 12/2017 | Mukherjee et al. | |
| 2018/0011988 A1 | 1/2018 | Ziegler et al. | |
| 2018/0052964 A1 | 2/2018 | Adelson et al. | |
| 2018/0085540 A1 | 3/2018 | Dantsker et al. | |
| 2018/0125365 A1 | 5/2018 | Hunter et al. | |
| 2018/0161530 A1 | 6/2018 | Ganton et al. | |

FOREIGN PATENT DOCUMENTS

| | | |
|---|---|---|
| EP | 1992381 A1 | 11/2008 |
| EP | 3228345 A1 | 10/2017 |
| WO | WO/1995/022365 A1 | 8/1995 |
| WO | WO 99-64095 A2 | 12/1999 |
| WO | WO/1999/063901 A1 | 12/1999 |
| WO | WO 2001/097889 A2 | 12/2001 |
| WO | WO 2002/000281 A2 | 1/2002 |
| WO | WO/2003/063754 A1 | 8/2003 |
| WO | WO 2005/034833 A2 | 4/2005 |
| WO | WO/2009/003989 A1 | 1/2009 |
| WO | WO 2014/106056 A2 | 7/2014 |
| WO | WO/2016/043601 A1 | 3/2016 |
| WO | WO/2017/005605 A1 | 1/2017 |
| WO | WO/2017/051389 A1 | 3/2017 |
| WO | WO/2017/129521 A1 | 8/2017 |
| WO | WO/2017/141194 A1 | 8/2017 |
| WO | WO/2017/176693 A1 | 10/2017 |
| WO | WO/2017/176704 A1 | 10/2017 |
| WO | WO/2017/180980 A1 | 10/2017 |
| WO | WO/2017/189712 A1 | 11/2017 |
| WO | WO/2018/128976 A1 | 7/2018 |
| WO | WO2018/134552 A1 | 7/2018 |
| WO | WO/2018/134553 A1 | 7/2018 |

(56) References Cited

FOREIGN PATENT DOCUMENTS

OTHER PUBLICATIONS

Wikipedia, "Wireless Repeater", Available at https://en.wikipedia.org/wiki/Wireless_repeater, Jan. 8, 2015, 2 pages.
AstraZeneca, "Tudorza Pressair, aclidinium bromide inhalation powder", www.tudorza.com © 2015, accessed Sep. 8, 2015, 24 pages.
Aradigm Corporation, "AERx Drug Delivery System", www.Aradigm.com, © 2015, accessed Sep. 8, 2015, 6 pages.
Lippincott Williams & Wilkins, "Analgesic Efficacy of Inhaled Morphine in Patients after Bunionectomy Surgery", www.anesthesiology.pubs.asahg.org/journal.aspx, © 2003, accessed Sep. 8, 2015, 22 pages.
Alexza Pharmaceuticals, Inc., "Adasuve loxapine Inhalation Powder", www.adasuve.com, © 2013, accessed Sep. 8, 2015, 7 pages.
Josh Buesseler, "Propeller Health Inhaler Sensor, Asthma Event Data Sensor", https://www.behance.net/gallery/14490057/Propeller-Health-Inhaler-Sensor Published Feb. 12, 2014, accessed Jul. 26, 2016, 6 pages.

\* cited by examiner

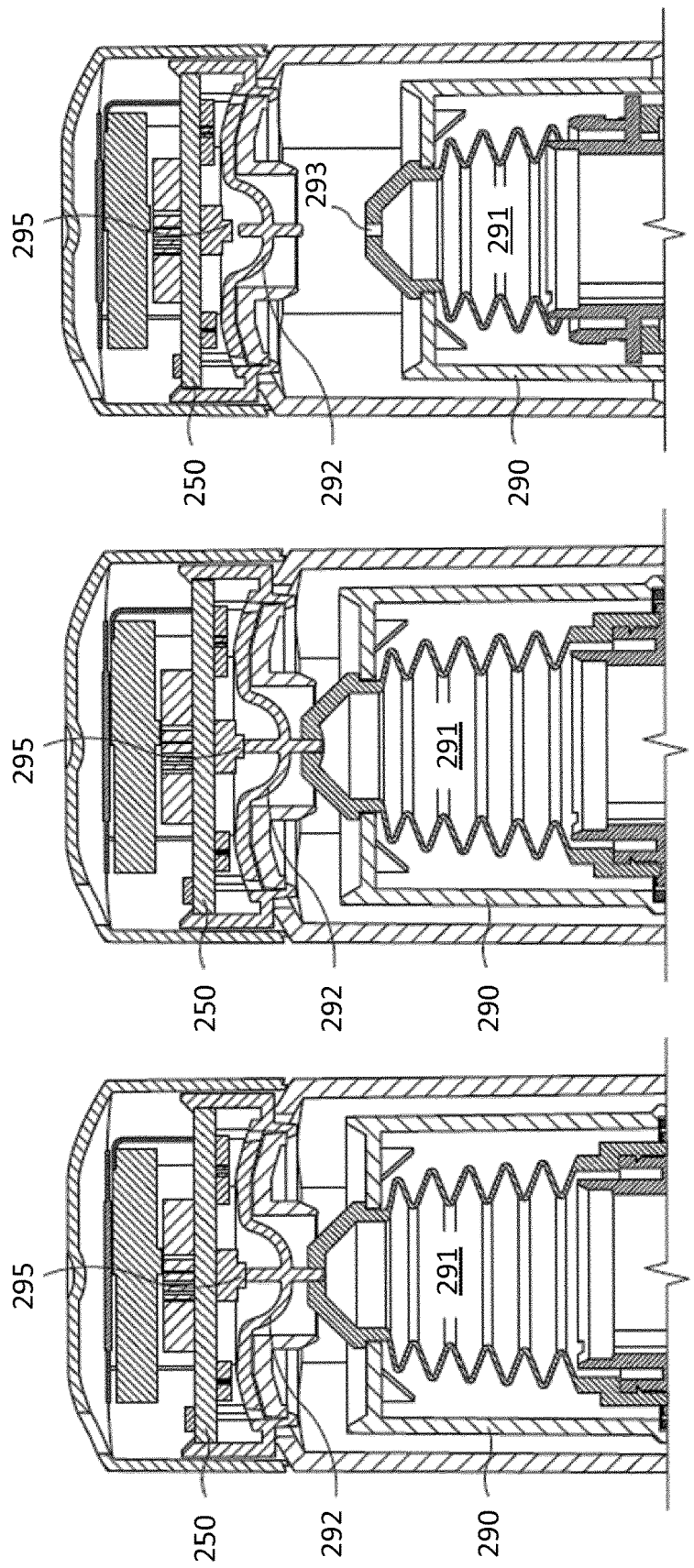

COMPLIANCE-ASSISTING MODULE FOR AN INHALER

CROSS-REFERENCE TO RELATED APPLICATIONS

This application is the National Stage Entry under 35 U.S.C. § 371 Patent Cooperation Treaty Application No. PCT/EP2015/069781, filed Aug. 28, 2015, which claims the benefit of U.S. Provisional Application No. 62/043,120, filed Aug. 28, 2014, the contents of which are incorporated by reference herein.

BACKGROUND

Inhalers or puffers may be used for delivering medication into the body via the lungs. They can be used, for example, in the treatment of asthma and chronic obstructive pulmonary disease (COPD). Types of inhalers may include metered dose inhalers (MDIs), dry powder inhalers (DPIs) and nebulizers.

A common problem faced in respiratory drug delivery is how to monitor patient adherence and compliance. Adherence deals with the patient following the prescription label, for example taking the prescribed number of doses per day. For example, if the prescription calls for two doses each day, and the patient is taking two doses a day, they are considered 100% adherent. If the patient is only taking one dose a day, they are only 50% adherent. In the latter case, the patient is not getting the treatment prescribed by their doctor.

Compliance, on the other hand, relates to how the patient uses their drug delivery device. If used in the manner recommended for effective treatment, they are 100% compliant. If not used properly however, they are less than 100% compliant. Use of a breath-actuated inhaler (e.g., a dry powder inhaler (DPI)) involves inhaling in a particular way; for example the inhalation may need to be long enough and hard enough to entrain a full dose of medicament. For some patients, for example children and the elderly, meeting the requirements for full compliance may be difficult. Failing to achieve 100% compliance can reduce the effectiveness of the prescribed medicament.

It is difficult for a patient to determine whether he or she inhaled the prescribed dose of medication and thus to verify compliance with the prescription. Especially for DPIs, a patient may not immediately notice that medication is being inhaled (e.g., because the particles are so small they may not be felt or tasted). A patient may learn of inhalation after seeing the medical effects and still may not know whether the amount of inhaled medication complies with the prescription.

SUMMARY OF THE INVENTION

The present disclosure generally relates to assisting patient compliance with medicament administration via an inhaler. For example, the disclosure may relate to the use of indicators to indicate when the inhaler is ready for releasing a dose and when the patient has inhaled sufficient to receive the recommended dose.

An inhaler may include a mouthpiece cover, a pressure sensor, a first indicator, and a second indicator. The first indicator may be a first light and the second indicator may be a second light. The first indicator may be a first state of a light and the second indicator may be a second state of the light. The first indicator may be configured to indicate based on a state of the mouthpiece cover. For example, the first indicator may be configured to illuminate based on an open state of the mouthpiece cover, where for example, medication may be ready for inhalation based on the open state of the mouthpiece cover. For example, medication may be transferred from a reservoir to a dosing cup based on the open state of the mouthpiece cover. The second indicator may be configured to indicate based on an output of the pressure sensor. For example, the second indicator may be configured to illuminate based on a pressure measurement in the mouthpiece or elsewhere in the inhaler exceeding a predetermined threshold. The predetermined threshold may be associated with administration of medication.

An inhaler may include a mouthpiece cover, a pressure sensor, and/or a light. The light may be configured to provide a first indication based on a state of the mouthpiece cover and a second indication based on an output of the pressure sensor. The first indication and the second indication may be different colors of the light. At least one of the first indication and the second indication may be a provided by flashing the light. The inhaler may include a dosing cup. A dose of medication may be released to the dosing cup based on a movement of the mouthpiece cover.

An inhaler may include a mouthpiece cover, a first light, and a second light. The first and second lights may be configured to indicate that the inhaler is ready for inhalation based on a state of the mouthpiece cover and to indicate inhalation. The first light may be configured to indicate that the inhaler is ready for inhalation based on the mouthpiece cover reaching an open state. The inhaler may include a dosing cup. A dose of medication may be released to the dosing cup based on a movement of the mouthpiece cover. The first light may indicate that the inhaler is ready for inhalation based on the inhaler being in an upright orientation.

The inhaler may include a sensor configured to provide an output based on air flow through a mouthpiece of the inhaler, which for example may be indicative of user inhalation. For example, the second light may be configured to indicate inhalation based on the sensor output. The second light may be configured to indicate inhalation based on a determination that an amount of inhaled medication has (e.g., and/or has not) reached a predetermined threshold (e.g., using the sensor). For example, the second light may be configured to flash to indicate that a sensor measurement has reached a first threshold (e.g., indicative of user inhalation) and to turn on based on a determination that a sensor measurement has reached a second predetermined threshold (e.g., indicative that an amount of inhaled medication has be delivered to the user).

BRIEF DESCRIPTION OF THE DRAWINGS

FIGS. 2A-C illustrate the top portion of the internal structure of an example inhaler.

DETAILED DESCRIPTION

Figure 1A:
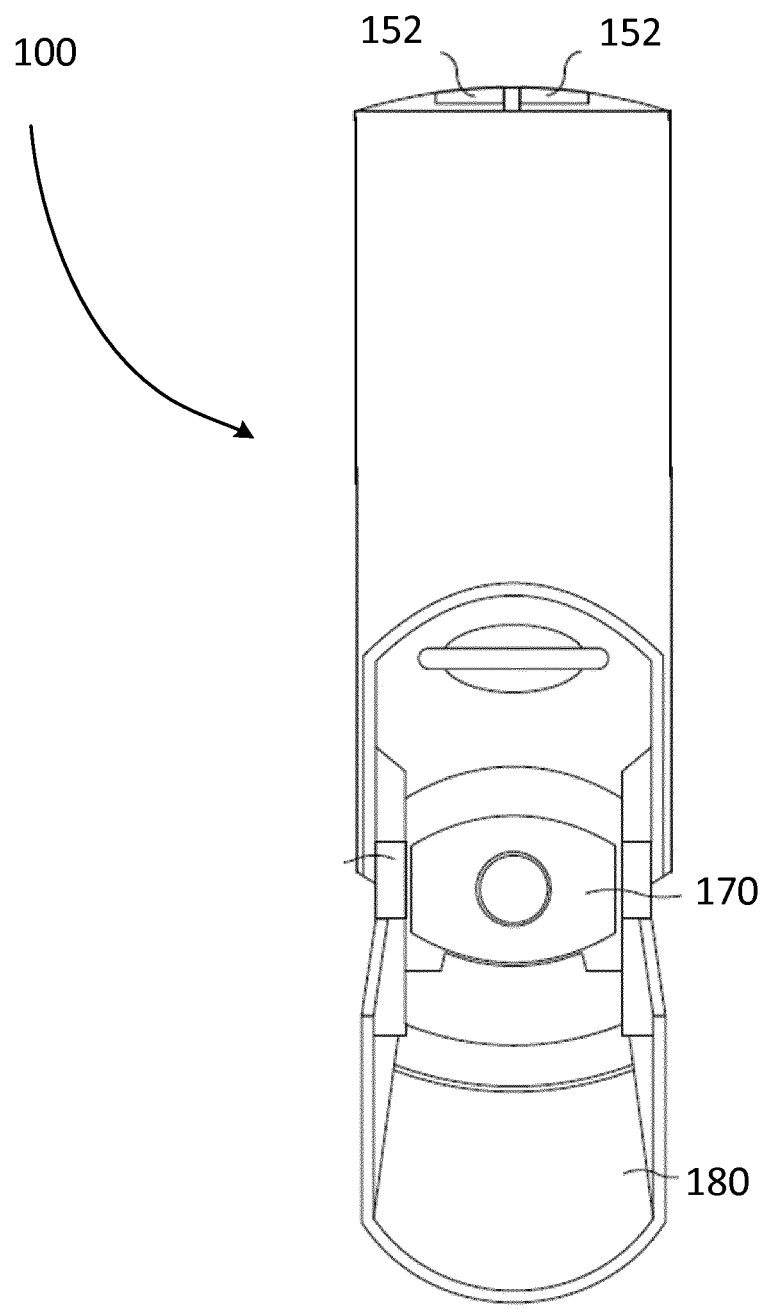
FIG. 1A illustrates an example of an inhaler with an indicator.

FIG. 1A illustrates an example inhaler 100 with an indicator. The inhaler 100 may have a mouthpiece 170. The inhaler 100 may have a cover 180 for the mouthpiece 170. The inhaler 100 may have indicators 152 (e.g., visual and/or audible indicators) to provide indication to a user. The indicators 152 may comprise two or more lights, for example, two lights as shown in FIG. 1A. The indicators 152 may be, for example, a single light. For example, the single light may provide multiple indications (e.g., a first color for a first indication, a second color for a second indication). The indicators 152 may comprise an audible indicator, such as a buzzer or speaker, for example. The indicators 152 may comprise one or more devices that provide haptic feedback. The indicators 152 may indicate the state of the inhaler 100 or the state of inhalation by a user. The indication may provide an instruction to its user, for example, such that the user knows when to start inhaling, continue inhaling, stop inhaling medication, a dose reminder, and/or the like. The indication may be performed by turning on one or more lights, turning off one or more lights, and/or flashing one or more lights. The indication may be performed through multiple colors or different types of flashing. For visual indicators, the indicators 152 may be located near the top of the inhaler 100 (for example, as shown in FIG. 1A). For example, the indicator 152 may be located near the top of the inhaler 100 such that a user can see the indicator easily while using the inhaler 100. The indicator 152 may include a screen that displays messages, pictographs, and/or colors for indication. The indicator 152 may indicate using sound or vibration. The indicator 152 may be capable of providing one or a mix of visual, audial, haptic indication.

Figure 1B:
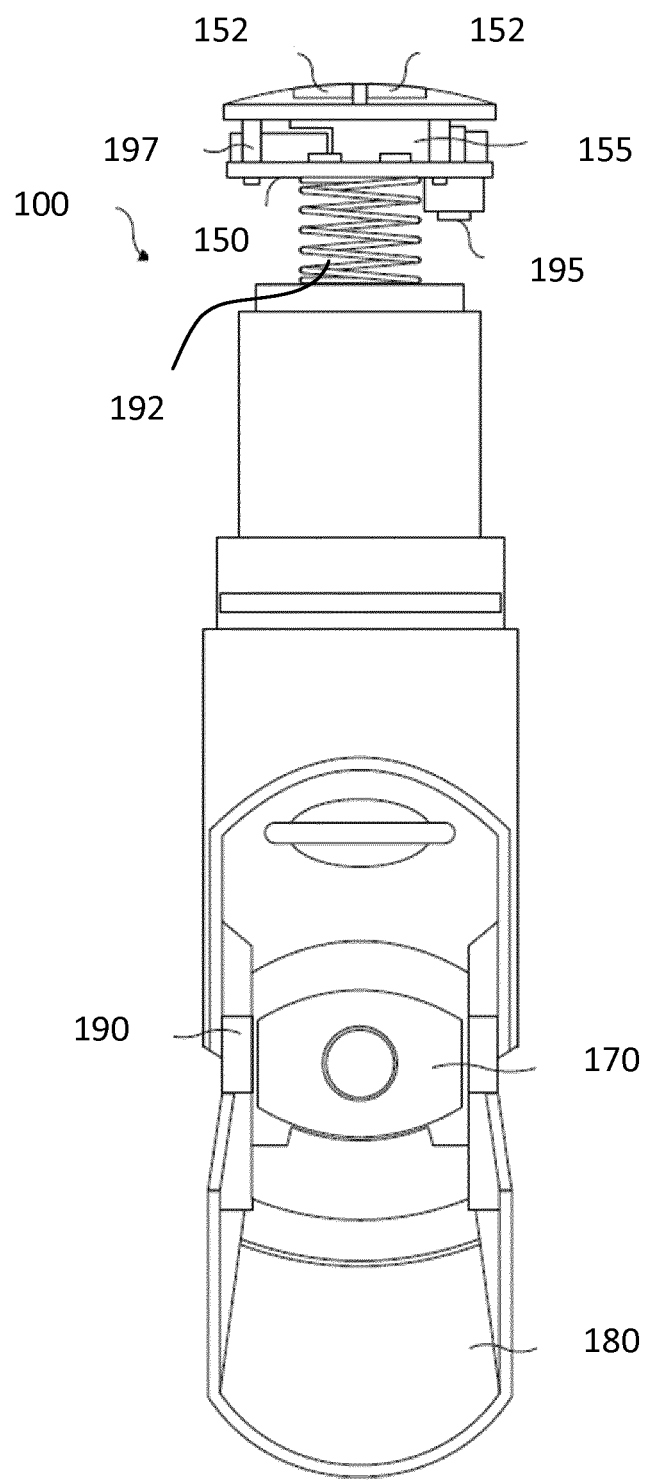
FIG. 1B illustrates an example of a partially-exploded view of an inhaler.

FIG. 1B shows a partially exploded view of the example inhaler 100. A mouthpiece 170 may be exposed by removing (e.g., swinging down) a cover 180. The downward motion of the mouthpiece 170 may push up a yoke 190. The yoke 190 may be a vertical bar that may reach an electronics module, or a PCB 150.

The PCB 150, which may carry a processor and transmitter, may be incorporated into the top of the inhaler 100 body. A collar 197 around the PCB 150 may be clipped onto the top of the yoke (not shown) towards the end of manufacture of the inhaler 100. This may be done following sterilization of parts of the inhaler body. This may be advantageous since the sterilization process may damage the sensitive electronics on the PCB 150.

The yoke 190 may be configured to rise when the mouthpiece cover 180 is opened. This may push the horizontal top part of the yoke 190 up to close the tactile switch 195. When the switch 195 is closed, an electrical connection may be formed between the PCB 150 and a battery 155, such as a coin cell, so that the PCB 150 may be powered up when the mouthpiece cover 180 is open. In an example, the PCB 150 may always be connected to the battery 155, but closing of the switch 195 (e.g., or activation of some other switching means, e.g. an optical sensor, an accelerometer or a Hall effect sensor) may wake the PCB 150 from a power-conserving sleep mode. For example, the PCB 150 may always be powered on and the circuit of the electronics module may be in standby, and opening of the mouthpiece cover 180 may wake up the circuitry of the electronics module (e.g., bring the electronics module out of sleep mode and into a full powered on state). Indicator light emitting diodes (LEDs) visible through (e.g., optionally colored) windows or light pipes shown on the exterior of the inhaler 100, for example, in a position visible to a user during dosing, may also be powered by battery 155 and may be controlled by a processor on the PCB. The indicator 152 may be used to provide information to a user and/or caregiver by indicating, for example with different color and flash combinations, that e.g. the mouthpiece cover is open (e.g., and therefore the inhaler is primed for dosing) and/or it is time to refill a prescription and/or that (e.g., according to processing of the pressure sensor readings) dosing is complete/has not been fully completed.

FIGS. 2A-C show an example arrangement of the top portion of the internal structure of an example inhaler (for example, the inhaler 100). A yoke 290, linked to a hinged mouthpiece cover (not shown) carries a bellows 291, made of, for example, a partially compliant material. FIG. 2A shows a bellows position when the cover is closed. A foot of a spring arm 292 may be received in a recess 293 in the upper wall of the bellows. The bottom of the recess 293 therefore may push on the lower surface of the foot such the spring arm is biased upwards. This may cause a head of the spring arm 292 to close a switch 295 which keeps a PCB 250 in sleep mode.

FIG. 2B shows the arrangement as opening of the cover is begun, when the yoke 290 and therefore the bellows 291 move slightly upwards. The spring arm 292 may remain contacting the switch 295 and the compliance of the bellows material may relieve any additional strain which would otherwise be put on the switch since the bottom of the recess 293 may bend to take the strain.

FIG. 2C shows the arrangement when the cover is fully open. The yoke 290 and bellows 291 may have moved down clear of the spring arm 292, which relaxes down away from switch 295. Switch 295 may therefore be opened, waking the PCB 250.

Figure 3:
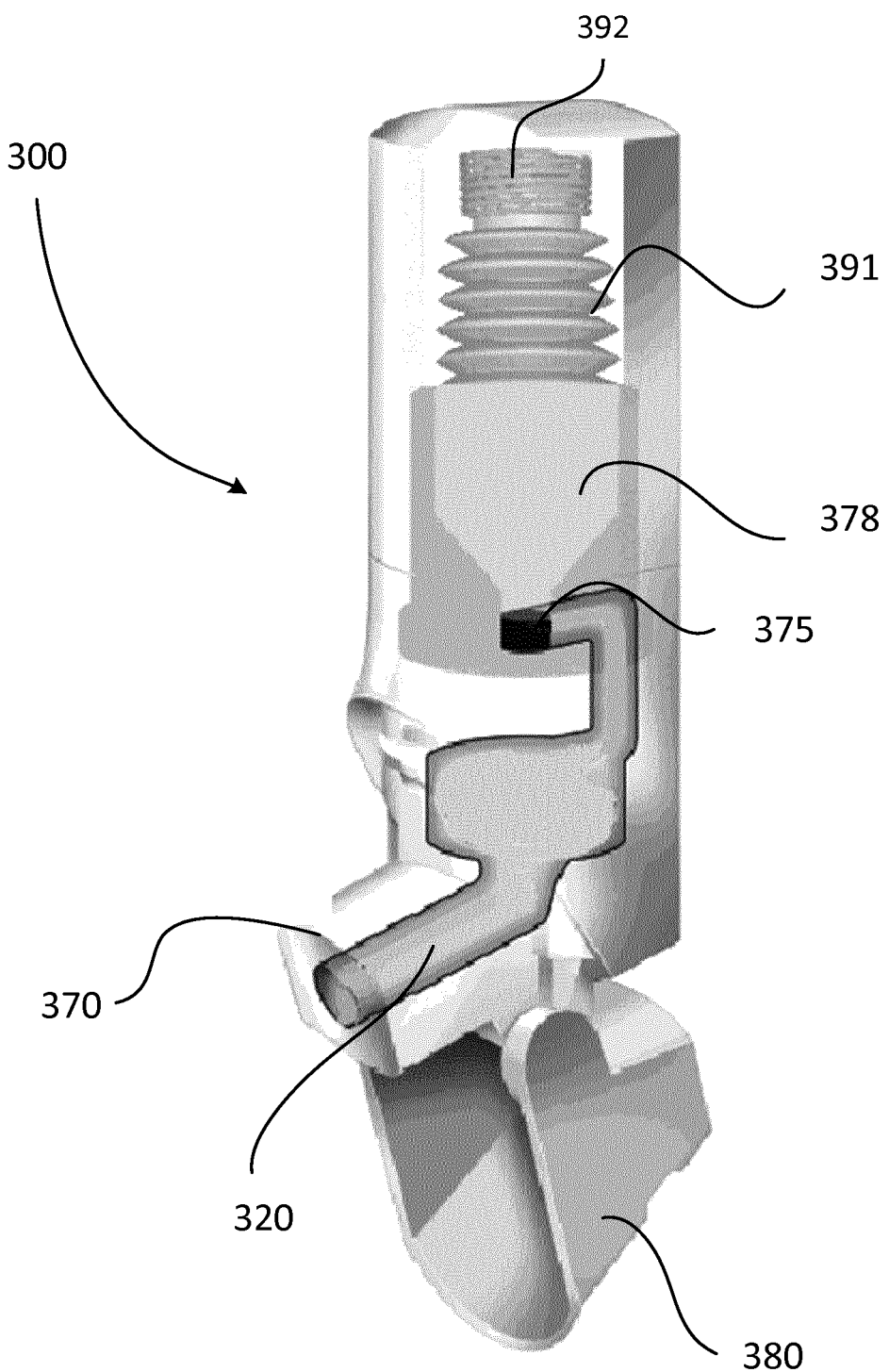
FIG. 3 illustrates an example internal structure of the inhaler.

FIG. 3 shows is an example diagram of an internal structure of an inhaler (e.g., the inhaler 100). For example, opening the mouthpiece cover may cause a transfer of medication from a reservoir to a dosing cup. The inhaler 300 may have a spring 392 and a bellows 391. The opening of the cover 380 may cause the compression or decompression of the spring 392. The spring 392 may compress the bellows 391 when the cover 380 opens from the mouthpiece 370. The compressed bellows 391 may provide pressure such that medication in a reservoir 378 flows to a dosing cup 375. Between the reservoir 378 and the dosing cup 375, there may be a hopper allowing the flow of medication. The hopper may slide to a position allowing the transfer of medication from the reservoir 378 into the dosing cup 375, for example, only when the cover 380 is open. The medication from the dosing cup may flow through a flow channel 320 when a user inhales using the mouthpiece 370.

Figure 4:
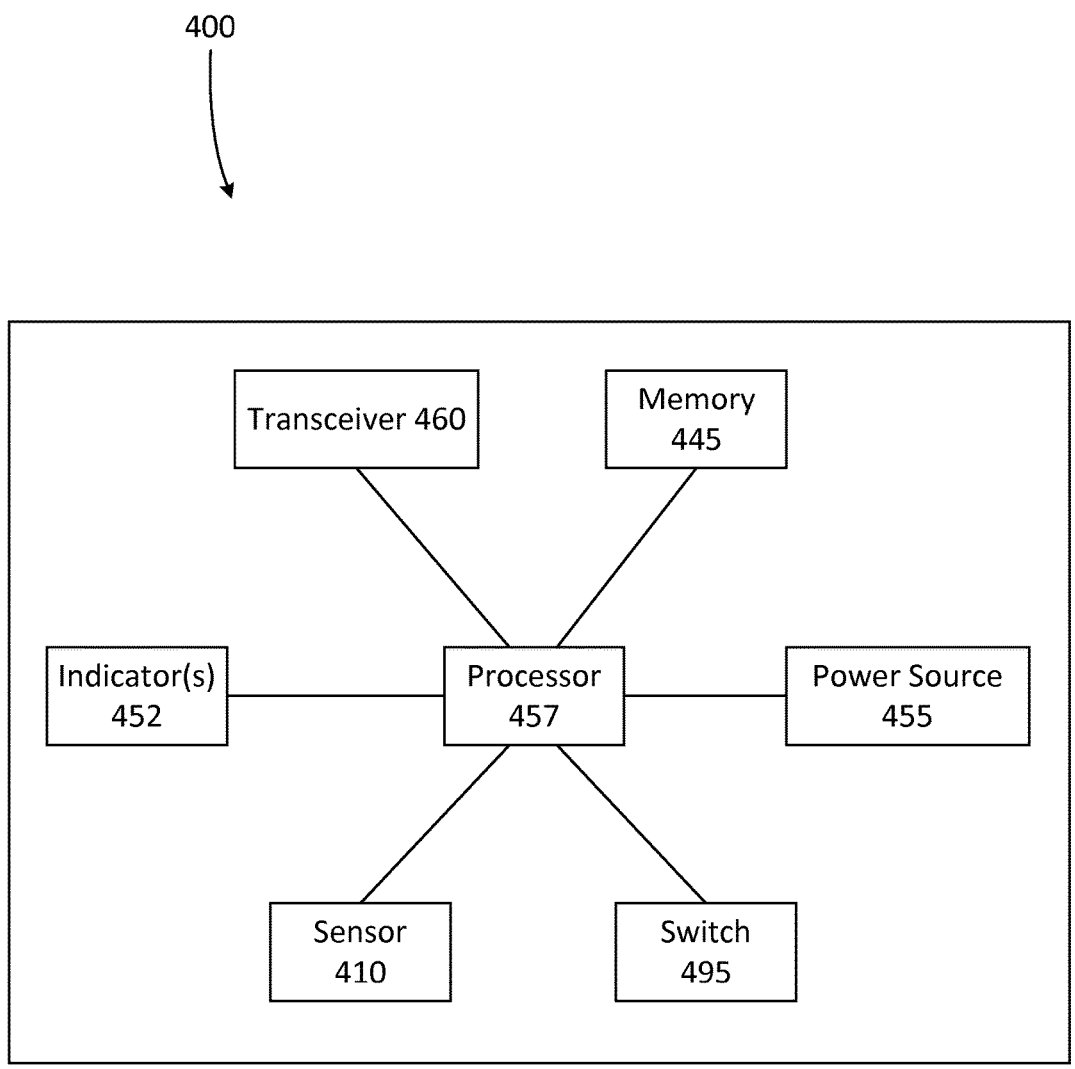
FIG. 4 is a schematic diagram of example electronics in an inhaler.

FIG. 4 is a schematic diagram of example electronics in an inhaler (e.g., the inhaler 100). The inhaler may comprise an electronics module 400. The electronics module 400 may have a processor 457, and a power source 455, a memory 445, indicator(s) 452, a switch 495, a sensor 410, and/or a transceiver 460. The processor 457 may be connected to each of the components. The switch 495 may be connected to a mouthpiece through a yoke, for example, as described in connection with FIG. 1B. The switch 495 is not limited to a mechanical switch, and it may, for example, be an electrical switch. The sensor 410 may provide information to the processor 457 about a pressure change (e.g., pressure difference) in the mouthpiece of the inhaler (e.g., or other part of the inhaler). For example, the sensor 410 may provide an instantaneous pressure reading to the processor or aggregated pressure reading over time. For example, the pressure reading may be in terms of Peak Inspiratory Flow, acceleration, total volume, total time, and/or the like. The pressure reading may be in terms of one or a combination of amplitude, acceleration, volume, and/or the like. The pressure reading (e.g., a pressure drop) may be measured elsewhere in the inhaler 700, and the inhaler 700 may calculate the flow in the mouthpiece accordingly. The pressure reading may be indicative of an amount of airflow through the mouthpiece of the inhaler, which for example, may be indicative of medication being inhaled by a user. As such, the sensor 410 may provide information to the processor 457 relating to the pressure reading, the amount of airflow through the mouthpiece (e.g., and/or other part of the inhaler), and/or medication being inhaled by a user. The processor 457 may make a determination (e.g., regarding one or more indicators) based on the pressure reading of the sensor 410. For example, the processor 457 may calculate the amount of air or medication inhaled based on the pressure reading provided by the sensor 410. The sensor 410 may have a separate processor to calculate the level of air or medication inhaled and provide it to the processor 457.

Based on the information received from the switch 495 and/or the sensor 410, the processor 457 may determine that the pressure reading (e.g., which may be indicative of medication inhaled by a user) reached a predetermined level. There may be a lookup table for the predetermined level with which the processor compares the pressure reading. When the predetermined level is reached, the processor 457 may send a signal to one or more indicator(s) 452 to indicate the state of the inhaler. The processor 457 may store in memory the pressure reading, a time stamp for the pressure reading, and/or information derived based on the pressure reading (e.g., medication dosed, medication administered to the user, medication administered in full to the user, air flow through the mouthpiece, etc.). For example, the processor 457 may access information (e.g., a lookup table for the predetermined level of medication) from, and store data in, any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The processor may access information from, and store data in, memory that is not physically located within the inhaler, such as on a server.

The processor 457 may comprise a microcontroller, a programmable logic device (PLD), a microprocessor, an application specific integrated circuit (ASIC), a field-programmable gate array (FPGA), or any suitable processing device, controller, or control circuit. The processor 457 may comprise an internal memory. The processor 457 may receive power from the power source 455, and may be configured to distribute and/or control the power to the other components in the inhaler 400. The power supply may be any suitable device for powering the inhaler. The switch 495 may not be connected to the processor 457, but the power source 455. The power source may be directly connected to one or more of the sensor 410, memory 445, the indicator(s) 452, and transceiver 460.

Indicators and an electronics module may be permanently attached to an inhaler. As shown in FIG. 1B, the indicators and the electronics module may be located at the top of the inhaler. In some embodiments, the electronics module may be located in a different location. For example, an inhaler may have a mountable cap to mount it on top of an inhaler. The cap may contain indicators and an electronics module to control the indicators. Indicators may be added to or removed from an existing inhaler without affecting its operation, for example, by using a mountable cap.

Figure 5B:
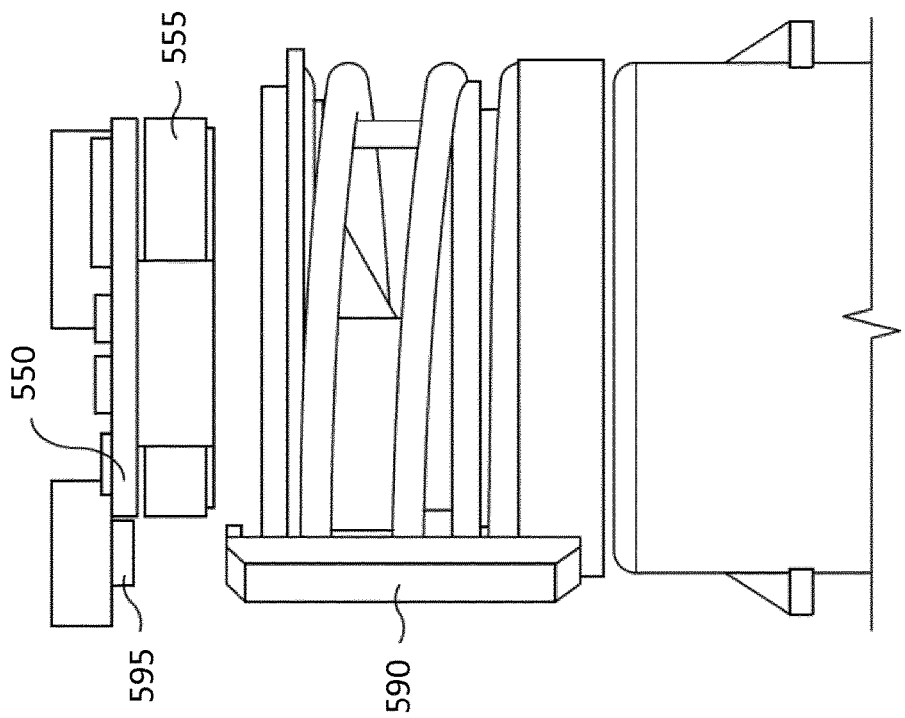
FIGS. 5A-C illustrate an example electronics module in an inhaler.
Figure 5A:
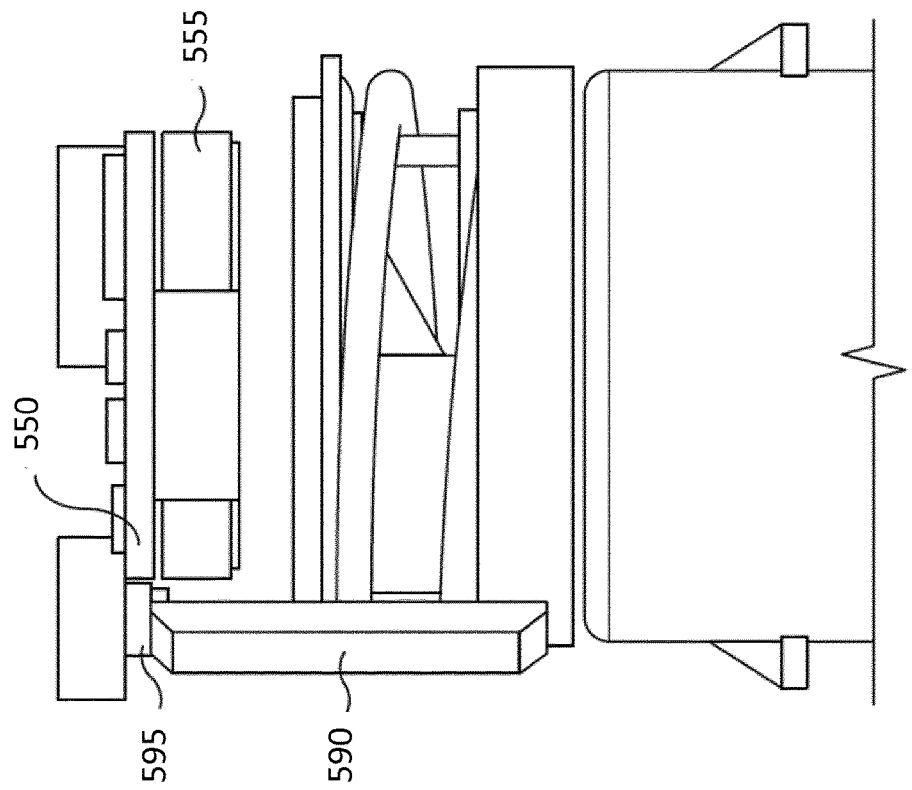

FIG. 5 illustrates how an electronics module 550 (e.g., compliance module) may be incorporated into the top of an inhaler (e.g., the inhaler 100) whether the indicators and electronics module are permanent or removable. The electronics module 550 may be an example of the electronics module 400 of FIG. 4. FIG. 5A shows an example default position of a yoke (e.g., retainer ring) 590, pushing up a tactile switch 595 to open it. With the switch 595 open, there may be no electrical connection between the compliance module 550 and a battery 555 such as a coin cell. FIG. 5B shows an example position of retainer ring 590 when the inhaler is primed for use, lowered with respect to the switch 595 to close it so that compliance module 550 is powered.

Figure 5C:
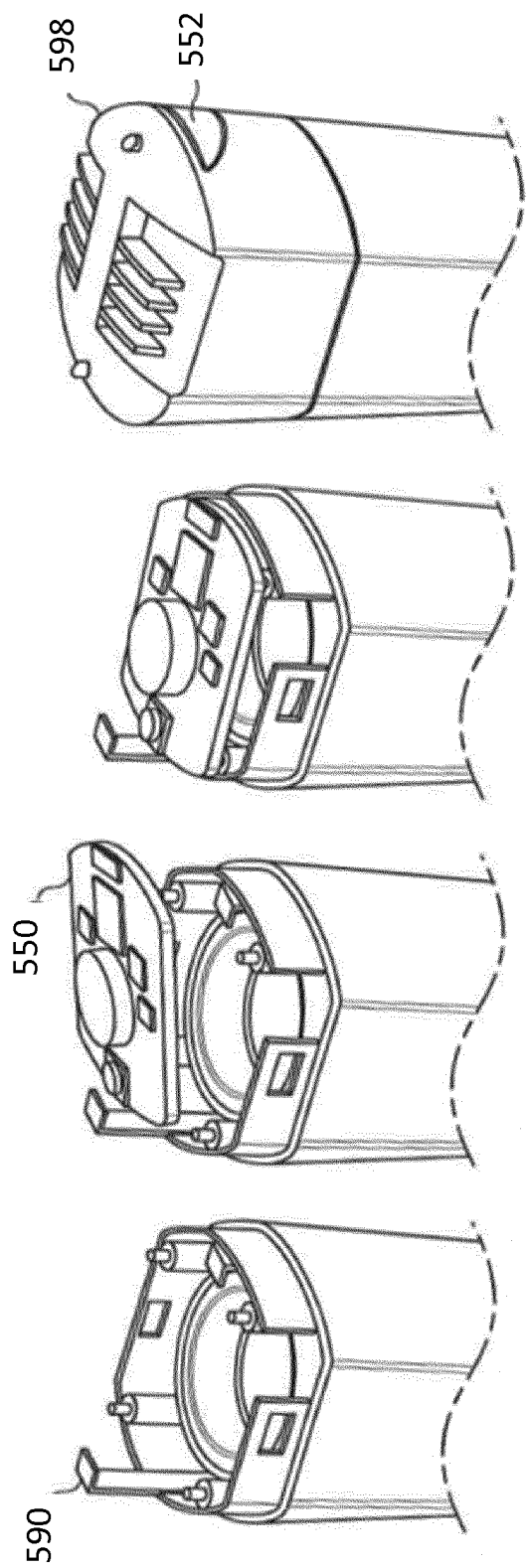

FIG. 5C illustrates the final stages of manufacture of the inhaler shown in FIGS. 5A and B. The compliance module 550 may be lowered onto the inhaler body then a cap 598 may be clipped in place. Like the previous examples, LED indicators 552 may be provided.

Example methods of using a sensor to detect inhalation are provided below. Although the examples below use a pressure sensor, specifically a barometric pressure sensor, an inhaler (e.g., the inhaler 100) may use other types of sensors to measure the inhalation.

A spirometer is an apparatus for measuring the volume of air inspired and expired by a patient's lungs. Spirometers measure ventilation, the movement of air into and out of the lungs. From the traces, known as spirograms, output by spirometers, it is possible to identify abnormal (e.g., obstructive or restrictive) ventilation patterns. Spirometers may use a variety of different measurement methods including pressure transducers, ultrasonic and water gauge.

In order to monitor the flows associated with breathing, a pressure sensor may be convenient because pressure information can be used to determine flow, which can then be used to determine volume.

Pressure sensors used for breath detection may measure the pressure difference across a section of the patient airway. This may be done using two connections, by tubing or other suitable conduit, to connect the sensor to the airway. It may also be possible to use a single connection to the airway, with the other port open to the atmosphere. A single port gauge type sensor can also be used if the pressure within the airway is measured both before and after flow is applied, the difference in readings representing the desired pressure drops across the air path resistance.

In addition to the differential (two port) type pressure sensors and the single port-gauge type sensors, with separate measurements made before and after use, absolute or barometric pressure sensors may be available. Barometric pressure sensors are referenced to vacuum. They are sometimes referred to as altimeters since altitude can be deduced from barometric pressure readings.

However, with miniaturization, including the introduction of MEMS and NEMS technologies, much improved sensors are now available. A MEMS barometric sensor may be capable of operation from 20 kPa to 110 kPa and can detect flow rates of less than 30 μm (liters per minute) when pneumatically coupled to a flow path having a known flow resistance.

Using a barometric sensor may enable use of the barometric pressure as a baseline throughout the measurement cycle, and thus it may address the uncertainty of other single port approaches.

Also, having knowledge of the local barometric pressure may provide some insight into patient lung function. It is suspected that changes in atmospheric pressure, such as those associated with approaching storm fronts, may have an effect on patient breathing, possibly even related to asthma and COPD events.

Barometric pressure sensors may already be in stressed condition, having an integral reference port sealed within the device under vacuum. This means that they have low hysteresis in the region of interest.

Due to the extremely small size and mass of their sensing elements, MEMS sensors may be capable of reacting to extremely small pressure changes. Some are capable of resolving pressure changes as low as 1 Pa.

For example, the Freescale MPL3115A2 MEMS barometer/altimeter chip (pressure 20 sensor) is digital, using an $I^2C$ interface to communicate pressure information to a host micro-computer.

MEMS pressure sensors can be packaged in metal. This may provide RF shielding and good thermal conductivity for temperature compensation.

MEMS pressure sensors are also low cost, exhibit low power consumption and are very small. This makes them especially suitable for use in portable and/or disposable devices which may, for example, be powered by batteries such as coin cells.

The small size of MEMS pressure sensors may make it easy to incorporate them into existing designs of inhalers. It may be easier to incorporate them in or close to a mouthpiece to more accurately measure the pressure change caused by a patient's inhalation or exhalation.

A miniature barometric pressure sensor can be connected directly to the patient airway using only a small hole to the air path which does not require tubing of any kind. This may reduce the possibility of moisture condensation and potential bacterial growth associated with elastomeric tubing. An internal seal, for example a gel seal, can be included to protect the sensor element from contamination.

Figure 6:
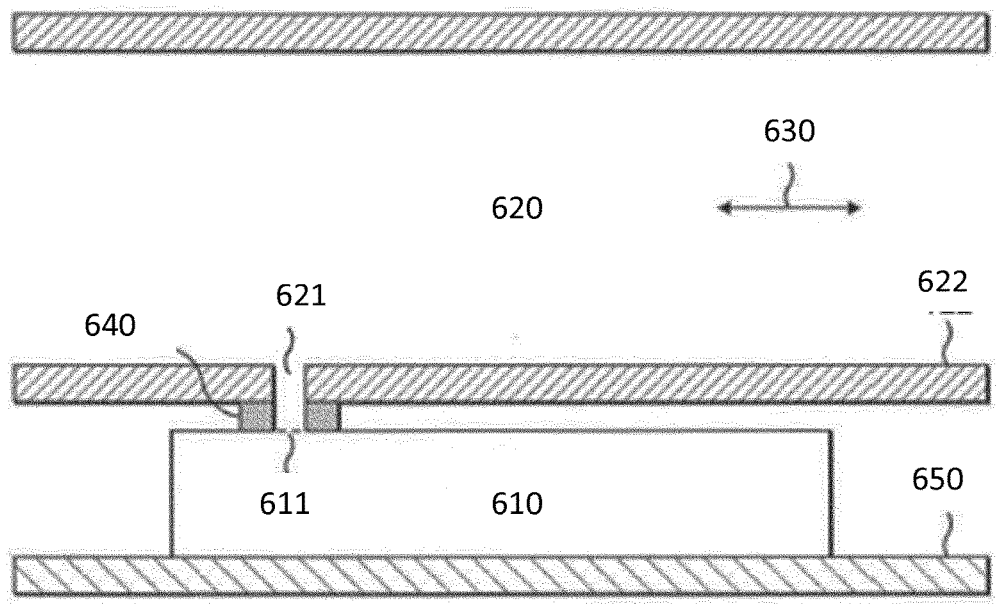
FIG. 6 shows a cross-section view of an inhaler mouthpiece with a sensor in an example configuration.

FIG. 6 shows a cross-section view of an inhaler mouthpiece with a sensor in an example configuration. A miniature barometric pressure sensor 610 may be placed against the flow channel 620 through which a patient breathes. Airflow may be substantially axial as indicated by arrow 630. The sensor port 611 may be sealed in line with an opening 621 in flow channel wall 622 by a pneumatic (e.g., airtight) seal 640. (Note that, so long as there is a pneumatic connection between the sensor port and the flow channel, the seal need not be completely airtight.) Sensor port 611 may comprise a filter, for example an air-permeable, water-impermeable filter. The flow channel and the seal may be formed by a two-shot molding process. The pressure sensor 610 may be mounted on a printed circuit board (PCB) 650 to provide connection to power sources and other electronics.

The miniature pressure sensor (e.g., the entire miniature pressure sensor) may be encapsulated within a chamber adjacent to the flow channel, for example, instead of positioning the seal 640 around the channel between opening 621 and sensor port 611. Pneumatic seal may be located outside of the sensor footprint and may extend all the way from the exterior of flow channel wall to the surface on which the sensor may be mounted (for example the component surface of a PCB).

MEMS sensors may be available with built-in temperature compensation. In an example, external thermal sensors may be used. In an example, external thermal sensors may not be used. Compensation may be provided right at the measurement site, increasing the accuracy of the compensation. A MEMS sensor with built-in temperature compensation may also act as a compact breath thermometer, providing further information to the patient and/or their caregiver. If the housing of the sensor is metal, then not only may the sensitive internal circuitry be isolated from RF fields, such as those associated with mobile phones or nearby disturbances, but the sensor may also rapidly equilibrate to the local temperature in order to provide optimum temperature compensation.

The addition of a miniature barometric pressure sensor anywhere in the airflow path through the inhaler or anywhere in fluid communication with the airflow path may enable compliance monitoring since such a miniature sensor may collect sufficient data to indicate whether or not the patient inhaled in an appropriate manner (e.g. hard enough and for long enough) to entrain a full dose of medicament. This information, combined with a signal originating from the dose metering system indicating that a bolus of medicament was made available to the flow channel through which the patient inhales prior to the inhalation, may be sufficient to confirm that a dose has been successfully administered.

It should be noted that due to their small size, MEMS pressure sensors can be used to monitor patient flow through, for example, nebulisers, DPIs or pMDIs, thus facilitating low cost compliance monitoring, in addition to/in place of adherence monitoring, which confirms device actuation. Said compliance monitoring could be implemented using an accessory device that couples to the dosing device through a small hole to the airway to be monitored, or in the dosing device itself. The small size, high performance and low cost of MEMS sensors may make them ideally suited to such applications where size and weight are major considerations for users who may have to carry their inhaler with them at all times.

If output from the miniature pressure sensor is digital, all low level signal processing can be done within the sensor, shielding it from outside interference. This makes it possible to work with signals of the order of tens of Pascals without much difficulty, something that traditional sensors with external circuitry would be challenged to do.

The sensor may, for example, be used in a breath actuated dry powder inhaler. These inhalers may be configured such that inhalation by the user through the mouthpiece results in an airflow through the device entraining dry powder medicament. The inhalation also may result in another airflow entering the inhaler from outside. The inhaler may comprise a swirl chamber in which the two airflows collide with one another and the chamber walls to break down aggregates of the dry powder medicament for more effective delivery.

For example, the sensor may be used in a breath actuated pressurized aerosol inhalers. These inhalers comprise a means for releasing a measured dose of medicament, the releasing means comprising a means for priming the device by applying a preload capable of actuating delivery means, a means for applying a resisting pneumatic force capable of preventing actuation of the delivery means and a release device capable of freeing the resisting pneumatic force to allow the preload to actuate the delivery means and dispense the medicament. The pneumatic resisting force can be established by mechanisms comprising, for example, a diaphragm, a piston cylinder, a bellows or a spring. Inhalation through a valve or past a vane mechanism allows the preload to actuate an aerosol valve to release medicament.

Adherence could be monitored for such inhalers by determining when the device is primed and/or when the aerosol valve opens. Again, the introduction of a MEMS barometric pressure sensor anywhere in the airflow path through the inhaler or anywhere in fluid communication with the airflow path, in combination with means for determining when the device has been primed and/or when the aerosol valve opens, may enable compliance monitoring.

Priming the device may result in both a preload being applied to the delivery means and a load being applied to an electronic switch. This switch may be connected to an input of the processor such that the processor receives an electronic pulse when the device is primed. Alternatively or additionally, an electronic switch may be arranged to be actuated by motion of the aerosol valve or of the valve or vane mechanism preceding the aerosol valve. This switch may be connected to an input of the processor such that the processor receives an electronic pulse when aerosol is released to the flow channel through which the patient inhales. The switch may be, for example, mechanical, optical, proximity based or an accelerometer.

It should be noted that because MEMS barometric pressure sensors respond to environmental barometric pressure, which can change over time, attention should be paid to the initial reading that any subsequent sensor output signal analysis is based upon. An automatic zero reading (e.g., tare) may be performed immediately prior to monitoring any inhalation signal. While it is possible for this value to change over time in response to changes in local environmental barometric pressure, it may not be expected to cause any issues if a treatment is completed within a few minutes. A second barometric chip may be used to keep track of barometric activity, allowing the primary chip to be used exclusively for breath detection.

The point at which dosing is complete (e.g., where lung volume peaks) may correspond to the point at which flow reverses direction. Thus, the processor may make a determination that dosing is complete when the data from the pressure sensor indicates that flow direction has reversed.

Not all processing needs to be done by the module. Any or all processing may be offloaded to an external data processing device. A wireless scheme (for example comprising a BLE module) may be used to transmit patient flow profiles to an app which could then calculate specific breathing parameters. The inhaler may thereby offload the processing required for such a task to, for example, a smart phone processor. This may facilitate the smallest form factors possible for the inhalers. A further advantage of this approach may be that software running on a smart phone may be changed more readily than software running on an inhaler.

The processor may provide the information gathered by the sensor and processed by the processor to a remote device through a transceiver. The transceiver is described in detail below. Although the examples below use wireless communication, an inhaler may communicate via other modes, including use of a wire.

The addition of transceiver may make it possible to monitor patient adherence and compliance and communicate such information, for example including patient flow profiles, to a user device, such as a smart phone, tablet, or computer. The information may be sent to a server, either directly from an inhaler or from a user device. From a user device data can be communicated to a caregiver's device, for example a doctor's personal computer (PC). This could be done using a wired connection, for example via a Universal Serial Bus (USB) port. Using wireless technology, it may be possible to communicate results to the outside world without interrupting the product housing in any significant way. Suitable wireless technologies could include, for example, WiFi technologies such as IEEE 802.11, Medical Body Area Network (MBAN) technologies such as IEEE 802.15, Near Field Communication (NFC) technologies, mobile technologies, such as 3G and 4G, and Bluetooth™ technologies, such as Bluetooth™ Low Energy (BLE). A wireless transceiver, for example in the form of a BLE chip, may be connected to the miniature sensor or integrated with it.

Such wireless connectivity may be used, for example, to report device actuation and/or sensed inhalation with date and time stamps in real time. This data may be processed externally and if the result of such processing is that it is determined that a prescription should be refilled, an alert may be sent to the patient and/or caregiver and/or pharmacist. Alerts may be provided via one or more user interfaces of the inhaler (for example an LED and/or a buzzer) or via text message or email. As an example, if no dosing report is received within a predetermined period following a scheduled dosing time, a reminder may be sent to the patient and/or caregiver. Alerts may also be generated for example if use frequency is exceeding a safe threshold.

The compliance module may communicate directly or indirectly with one or more of: a user device (such as a mobile phone e.g. a smartphone, a tablet, a laptop or a desktop computer) of a patient, or of a caregiver (such as a doctor, nurse, pharmacist, family member or carer), a server e.g. of a health service provider or inhaler or drug manufacturer or distributor or a cloud storage system. Such communication may be via a network such as the Internet and may involve a dedicated app, for example on the patient's smartphone.

Compliance monitoring means (such as one or more sensors, e.g. a device actuation sensor such as a mechanical switch to detect adherence and compliance reporting means, e.g. a miniature pressure sensor to detect sufficient flow for proper dose delivery) and compliance reporting means (such as a wireless transmitter or wired output port) may be included in a single module. This module may be sold as a separate inhaler accessory/upgrade for attachment to an existing or slightly modified design of inhaler. The compliance monitoring module may be incorporated into the inhaler during manufacture. The compliance monitoring module may be in a single physical unit. The compliance monitoring module may be in multiple units. In the case of an inhaler accessory version, the module may consist of one or more attachable units. In the case of a module incorporated into an inhaler, the individual components may be located in any suitable locations in or on the inhaler and need not be grouped together or connected any further than required for them to function.

Figure 7A:
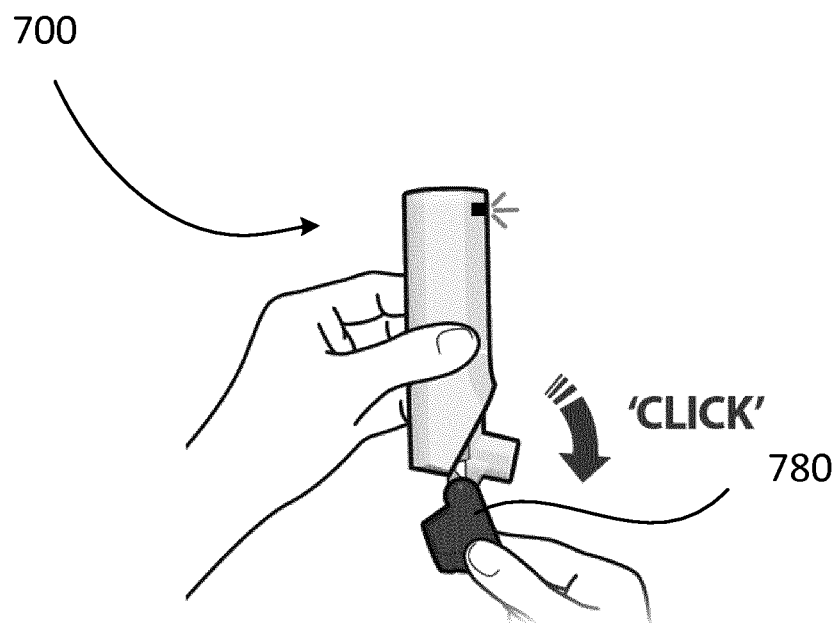
FIGS. 7A-F illustrate examples of an inhaler providing indications.
Figure 7B:
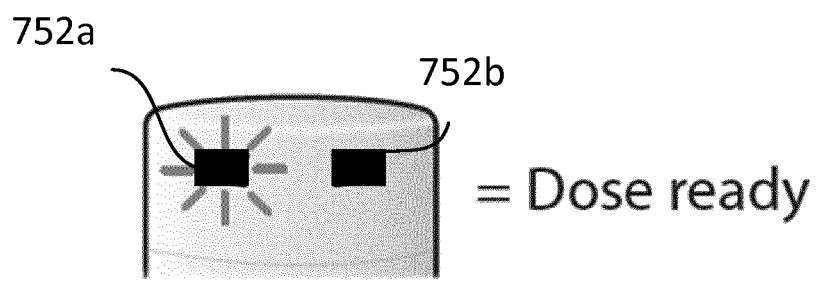

FIGS. 7A-F are example diagrams of various states of an inhaler 700 and its indications. FIGS. 7A-B are example diagrams that show an inhaler 700 indicating that a dose of medication is ready for inhalation. The inhaler 700 may be an example of the inhaler 100. When a user opens a mouthpiece cover 780, a dose may be ready. For example, a dose of medicament may be delivered from a reservoir (e.g., the reservoir 178) to a dosing cup (e.g., the dosing cup 175). The inhaler 700 may make a "click" sound and/or may illuminate one or more indicators 752 to indicate a "dose ready" state of the inhaler. For example, to indicate the "dose ready" state, the indicator 752a may illuminate and the indicator 752b may remain turned off, may be flashing, and/or may illuminate. The inhaler 700 may include a button that may be pressed to ready a dose of medicament either in addition to or in replacement of the opening of the cover 780. The inhaler 700 may be in a particular orientation (e.g., upright orientation) when opening the cover 780 or pressing a button to indicate the "dose ready" state.

Figure 7C:
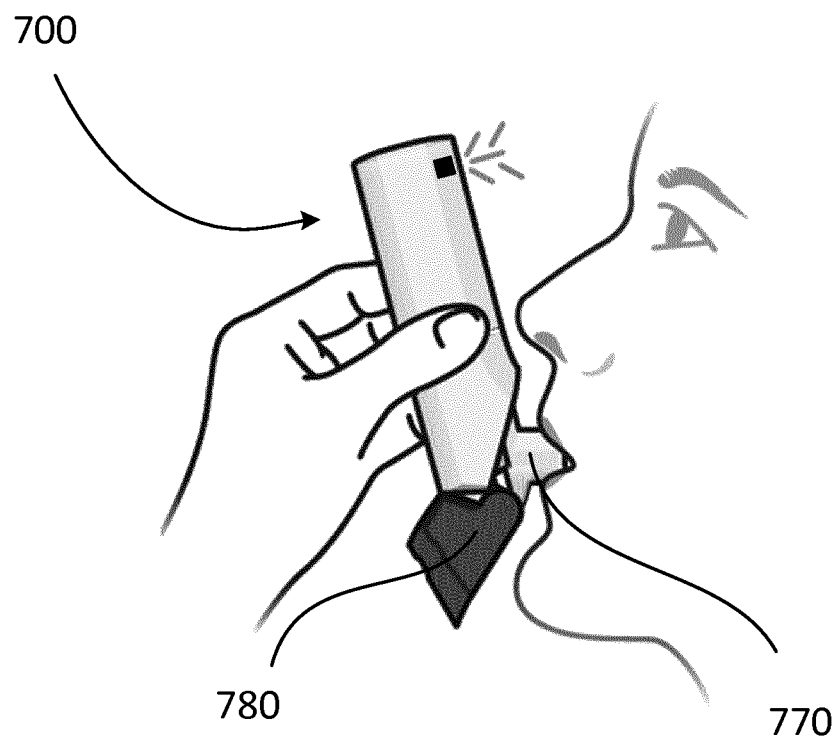
Figure 7D:
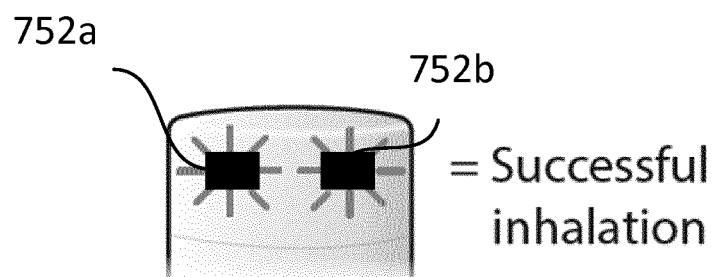

FIGS. 7C-D are example diagrams that show the inhaler 700 indicating a pressure measurement in the mouthpiece 770 exceeds a predetermined threshold (e.g., Peak Inspiratory Flow, acceleration, total volume, total time, and/or the like). Example methods of determining the amount of inhalation are provided herein, for example, as described in reference to FIGS. 4 and 6. The inhaler 700 may indicate that a pressure measurement exceeds a predetermined threshold, which for example, may indicate that the user successfully inhaled the medication. For example, the pressure measurement (e.g., a pressure drop) may be measured elsewhere in the inhaler 700, and the inhaler 700 may calculate the flow in the mouthpiece accordingly. The inhaler 700 may have indicators to make a sound, vibrate, or illuminate to indicate successful inhalation. For example, both the indicator 752a and the indicator 752b may illuminate for such indication. For example, the indicator 752a may stay on and the indicator 752b may be turned off.

Figure 7E:
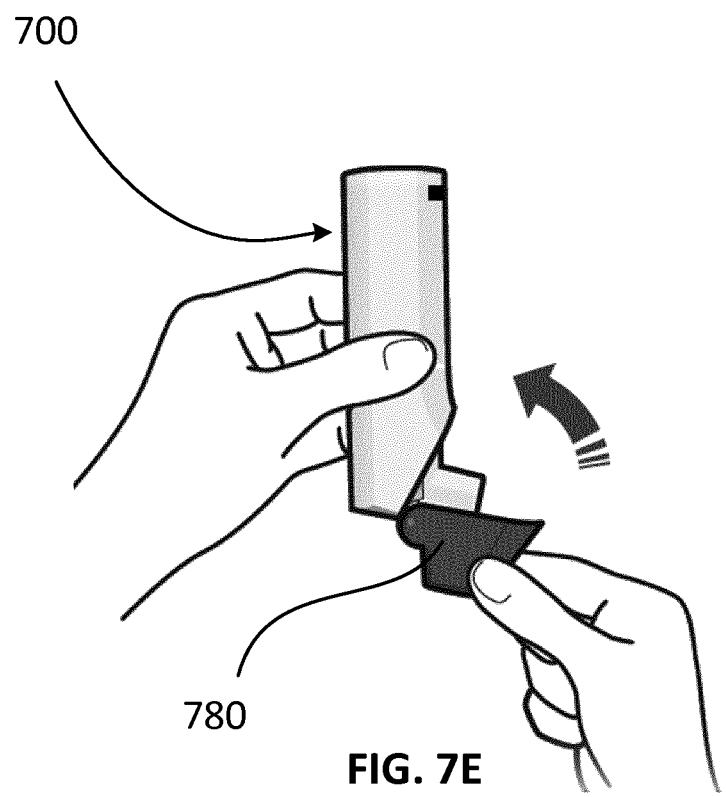
Figure 7F:
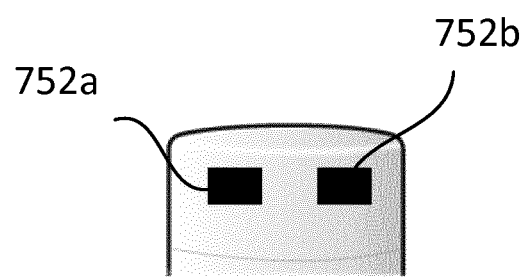

FIGS. 7E-F are example diagrams that show the inhaler 700 indicating that the inhaler 700 is off. The inhaler 700 may indicate that the inhaler is off, for example, when a user closes the cover 780. The inhaler 700 may make a "click" sound and/or turn off both indicators 752a and 752b to indicate that the inhaler 700 is off (e.g., that the electronics module 550 is powered off). Although not illustrated, the inhaler 700 may provide a dose reminder indication using of or more of the indicators 752a, 752b. For example, the inhaler may indicate that it is time for a user to take a dose of medication. For example, the inhaler 700 may illuminate the indicator 752a and/or the indicator 752b in a specific light pattern, color, etc. to indicate to the user that it is time for a user to take a dose of medication. The inhaler 700 may comprise a timer circuit that, when expires, causes the inhaler 700 to use one or more indicators to indicate that it is time for a user to take a dose of medication.

Figure 8:
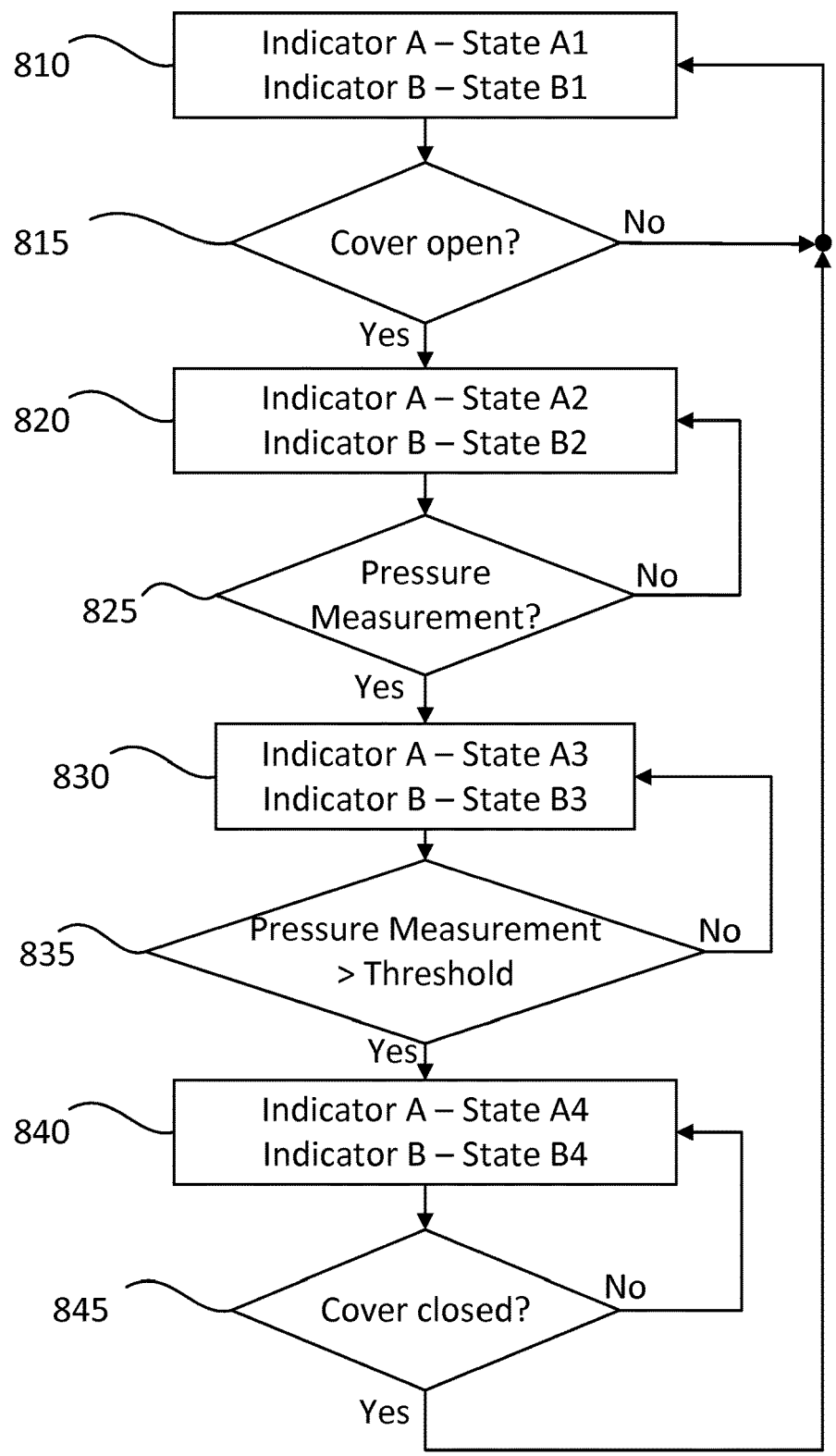
FIG. 8 is a flowchart illustrating an example compliance assisting methods with at least two indicators (e.g., two lights).

FIG. 8 is an example flow diagram that illustrates the inhaler's states (e.g., the inhaler 100) through operation. For example, the inhaler may comprise two indicators, an indicator A and an indicator B (e.g., a first light and a second light). At 810, an inhaler cover (e.g., cover 180) may be closed and/or the indicators A and B are in states A1 and B1, respectively. For example, indicators A and B may be off in states A1 and B1. When the inhaler (e.g., through a processor inside the inhaler) detects that the cover is open at 815, the indicators may be in (e.g., changed to) states A2 and B2 at 820. For example, the indicator A may illuminate in state A2, and the indicator B may be off in state B2. When the inhaler detects a pressure measurement (e.g., at a first threshold) of the inhaler (e.g., via a pressure sensor) at 825, the indicators may be in state A3 and B3 at 830. For example, the indicator A may illuminate in state A3, and the indicator B may be flashing in state B3. The pressure measurement may be indicative of (e.g., caused by) the user inhaling medication. The pressure measurement may be a pressure reading in the mouthpiece or elsewhere in the inhaler.

When the inhaler detects that the pressure measurement of the inhaler exceeds a predetermined amount at 835 (e.g., which may be indicative of a full dose of medication being administered to the user), the indicators A and B may be in state A4 and B4 at 840. For example, the indicator A may illuminate in state A4 and the indicator B may illuminate in state B4. If the inhaler detects that the cover is closed at 845, then the indicators A and B may be in state A1 and B1 at 810. For example, the indicators A and B may be off in states A1 and B1. In one or more embodiments, 825 and 830 may be omitted such that the inhaler may proceed to 835 from 820.

Example state diagrams may include the states A1, B1, A2, B2, A3, B3, A4, and B4 of the indicators A and B being in any combination of an off state, an on state, and/or a flashing state. Moreover, if the indicator is a light, the on state and/or flashing state may be characterized by the light being illuminated in one or more of a plurality of colors. The indicator may use different patterns of flashing. For example, example state diagrams are provided in Table 1 below:

TABLE 1

Example configurations of inhaler indicators

| Example State Diagram | State A1 | State B1 | State A2 | State B2 | State A3 | State B3 | State A4 | State B4 |
|---|---|---|---|---|---|---|---|---|
| Ex. 1 | Off | Off | On | Off | On | Off | On | On |
| Ex. 2 | Off | Off | On | Flashing | On | Flashing | On | On |
| Ex. 3 | Off | Off | On | On | On | On | On | Off |
| Ex. 4 | Off | Off | On | Flashing | On | On | On | Off |

In example 1, indicator A is off in state A1 (e.g., when the cover is closed), on in state A2 (e.g., to indicate that a dose is ready), on in state A3 (e.g., while the user is inhaling), and on in state A4 (e.g., when the dose has been administered). In example 1, indicator B is off in states B1, B2, and B3, and on in state B4. In example 2, indicator A is off in state A1, and on in states A2, A3, and A4. In example 2, indicator B is off in state B1, flashing in states B2 and B3, and on in state B4. In example 3, indicator A is off in state A1, and on in states A2, A3, and A4. In example 3, indicator B is off in state B1, on in states B2 and B3, and off in state B4. In example 4, indicator A is off in state A1, and on in states A2, A3, and A4. In example 4, indicator B is off in state B1, flashing in state B2, on in state B3, and off in state B4. There may be other methods of indicating the states. For example, the indicators may include multi-light and/or multi-color configurations.

Figure 9:
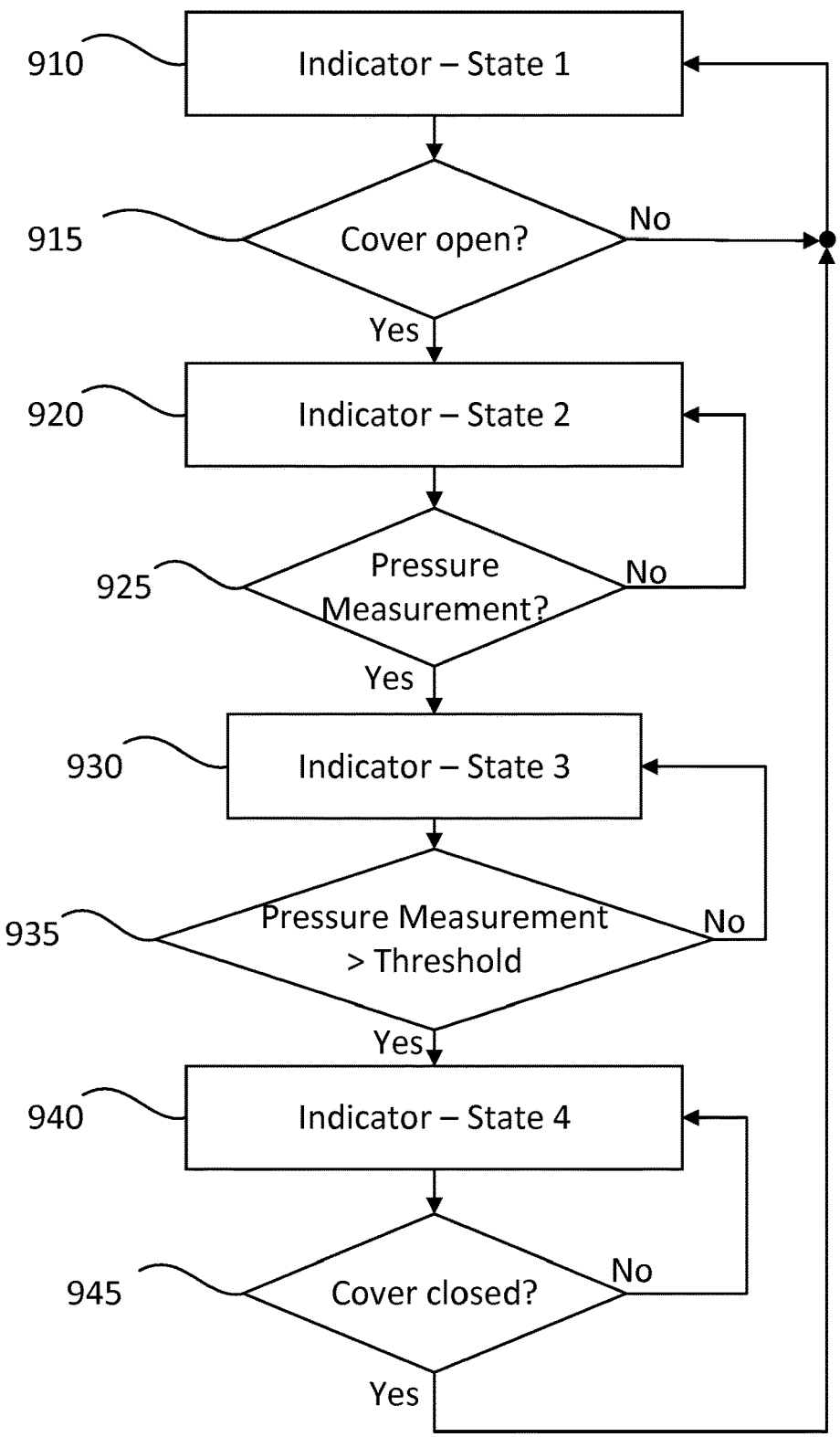
FIG. 9 is a flowchart illustrating an example compliance assisting method with a single indicator (e.g., a single light).

An inhaler (e.g., the inhaler 100) may have a single indicator, which for example, may be a light. The indicator light may have multiple colors and/or multiple modes of indication. For example, the indicator light may be on, off, flashing, and/or illuminate in multiple colors. The indicator light may use different patterns of flashing. FIG. 9 is an example flow diagram of an inhaler with a single indicator (e.g., indicator light). At 910, the cover of the inhaler may be closed and the indicator light is in state 1. For example, the indicator light may be off in state 1. When the inhaler (e.g., through a processor inside the inhaler) detects that the cover is open at 915, the indicator may be in (e.g., changed to) state 2 at 920. For example, the indicator may illuminate or flash in state 2. When the inhaler detects a pressure measurement (e.g., at a first threshold) of the inhaler (e.g., via a pressure sensor), the indicator may be in state 3 at 930. For example, the indicator may illuminate or flash in state 3. The pressure measurement may be indicative of (e.g., caused by) the user inhaling medication.

When the inhaler detects that the pressure measurement of the inhaler exceeds a predetermined amount at 935 (e.g., which may be indicative of a full dose of medication being administered to the user), the indicator may be in state 4 at 940. For example, the indicator may illuminate in state 4. If the inhaler detects that the cover is closed at 945, then the indicator may be in state 1 at 910. For example, the indicator may be off in state 1. In one or more embodiments, 925 and 930 may be omitted such that the inhaler may proceed to 935 from 920.

The indicator may be on, off, flash, and/or illuminate in different colors to indicate different states. For example, indicator may indicate state 2 with green and state 4 with blue.

Example state diagrams may include the states A1, B1, A2, B2, A3, B3, A4, and B4 of the indicator being in any combination of an off state, an on state, and/or a flashing state. Moreover, if the indicator is a light, the on state and/or flashing state may be characterized by the light being illuminated in one or more of a plurality of colors. The indicator may use different patterns of flashing. For example, example state diagrams are provided in Table 2 below:

TABLE 2

Example configurations of an inhaler indicator

| Example State Diagrams | State 1 | State 2 | State 3 | State 4 |
|---|---|---|---|---|
| Ex. 1 | Off | Flash | Flash | On |
| Ex. 2 | Off | On | On | Off |
| Ex. 3 | Off | On - Color 1 | On - Color 1 | On - Color 2 |
| Ex. 4 | Off | On - Color 1 | Flash | On - Color 2 |
| Ex. 5 | Off | Off | Off | On |
| Ex. 6 | Off | On - Color 1 | On - Color 2 | On - Color 3 |

In example 1, the indicator is off in state A1 (e.g., when the cover is closed), flashing in state 2 (e.g., to indicate that a dose is ready), flashing in state 3 (e.g., while the user is inhaling), and on in state 4 (e.g., when the dose has been administered). In example 2, the indicator is off in state 1, and on in states 2, 3, and off in state 4. In example 3, the indicator is off in state 1, on in a first color in states 2 and 3, and on in a second color in state 4. In example 4, the indicator is off in state A1, on in a first color in state 2, flashing in state 3, and on in a second color in state 4. In example 5, the indicator is off in states 1, 2, and 3, and on in state 4. In example 6, the indicator is off in state 1, on in a first color in state 2, on in a second color in state 3, and on in a third color in state 4. There may be other methods of indicating the states. For example, the indicators may include multi-light and/or multi-color configurations.

The inhaler (e.g., the inhaler 100 may determine that the reservoir is empty, for example, via a dose counter. The dose counter may be mechanical and/or electrical. For example, the electronics module of the inhaler may determine that the reservoir is empty. In an example, the dose counter may be configured to count down the number of available doses based on actuations of the cover, which for example, may correspond to dispensing of medication into a dosing cup. When the inhaler determines that the reservoir is empty and when the cover is subsequently opened, the inhaler may leave the indicator(s) in the off state. This, for example, may indicate to the user that the inhaler is not ready for inhalation because the inhaler is out of medication. The inhaler may indicate that the reservoir is empty using one or more of the indication techniques described herein (e.g., sold light, colored light, flashing light, one or more indicators, etc.).

Although not illustrated, the examples provided herein (e.g., with reference to FIGS. 8-9 and the associated description and examples) may include one or more additional indications. For example, the inhaler may further provide a dose reminder indication to the user. The dose reminder indication may indicate that it is time for the user to take a dose of medication. For example, the inhaler may use one or more indicators (e.g., lights, sounds, haptic feedback, etc.) to provide a dose reminder to the user.

Although described primarily with reference to visual indicators (e.g., one or more lights and/or light states), one or more of the embodiments/examples described herein may comprise other indicators. For example, the indicators may comprise visual indicators (e.g., one or more lights and/or light states), audible indicators (e.g., one or more buzzers/speakers and/or sounds), and/or haptic feedback indicators (e.g., one or more haptic feedback devices and/or haptic feedback states/operations).

What is claimed:

1. An inhaler comprising:
   a mouthpiece cover;
   a dosing cup;
   a medication reservoir configured to deliver a dose of medication into the dosing cup upon the mouthpiece cover moving from a closed position to an open position;
   a pressure sensor;
   a light; and
   a processor configured to control the light to be in a first state when the mouthpiece cover is in the closed position, a second state upon medication being delivered from the medication reservoir to the dosing cup, and a third state based on an output of the pressure sensor.

2. The inhaler of claim 1, wherein the first state is off, the second state is on, and the third state is off.

3. The inhaler of claim 1, wherein the first state is off, the second state is on, and the third state is flashing.

4. The inhaler of claim 1, wherein the first state is off, the second state is flashing, and the third state is on.

5. The inhaler of claim 1, wherein the third state is indicative of a successful inhalation from the inhaler.

6. The inhaler of claim 1, wherein the processor is configured to control the light to be in the third state when the output received from the pressure sensor exceeds a predetermined threshold.

7. The inhaler of claim 6, wherein the output of the pressure sensor comprises a pressure measurement corresponding to an amount of airflow through a mouthpiece of the inhaler.

8. The inhaler of claim 1, wherein the processor is configured to control the light to be in a fourth state based on a number of actuations of the mouthpiece cover from the closed position to the open position.

9. The inhaler of claim 8, wherein the fourth state is indicative of no doses of medication remaining in the inhaler.

10. The inhaler of claim 1, wherein the processor is configured to control the light to be in a fourth state to indicate that it is time for the user to take the dose of medication.

11. A method of signaling states of an inhaler to a user, the method comprising:
- controlling a light of the inhaler to be in a first state when a mouthpiece cover of the inhaler is in a closed position;
- delivering a dose of medication into a dosing cup upon the mouthpiece cover moving from the closed position to an open position;
- controlling the light to be in a second state upon the dose of medication being delivered into the dosing cup;
- receiving a signal from a pressure sensor of the inhaler, the signal indicative of a drop of pressure within the inhaler;
- determining that the signal exceeds a predetermined threshold; and
- controlling the light to be in a third state based on the signal exceeding the predetermined threshold.

12. The method of claim 11, wherein the first state is off, the second state is on, and the third state is off.

13. The method of claim 11, wherein the first state is off, the second state is on, and the third state is flashing.

14. The method of claim 11, wherein the first state is off, the second state is flashing, and the third state is on.

15. The method of claim 11, wherein the third state is indicative of a successful inhalation.

16. The method of claim 11, wherein the signal from the pressure sensor comprises a pressure measurement corresponding to an amount of airflow through a flow channel of the inhaler.

17. The method of claim 11, further comprising controlling the light to be in a fourth state based on a number of actuations of the mouthpiece cover from the closed position to the open position.

18. The method of claim 17, wherein the fourth state is indicative of no doses of medication remaining in the inhaler.

19. The method of claim 11, further comprising controlling the light to be in a fourth state to indicate that it is time for the user to take the dose of medication.

20. The method of claim 11, further comprising delivering the dose of medication to the user via a flow channel of the inhaler when the user inhales from a mouthpiece of the inhaler.

* * * * *